United States Patent [19]

Peterson

[11] 4,316,464

[45] Feb. 23, 1982

[54] POULTRY VACCINATION SYSTEM

[75] Inventor: Walter L. Peterson, Gainesville, Ga.

[73] Assignee: Select Laboratories, Inc., Gainesville, Ga.

[21] Appl. No.: 241,495

[22] Filed: Mar. 9, 1981

[51] Int. Cl.$^3$ .......... A61M 11/00

[52] U.S. Cl. .......... 128/253; 128/213 R

[58] Field of Search .......... 128/223, 253, 207.19, 128/200.14, 200.18, 200.21, 200.22, 200.23, 213 R; 119/158, 159, 160, 1, 156

[56] References Cited

U.S. PATENT DOCUMENTS

| | | | |
|---|---|---|---|
| 974,252 | 11/1910 | Fish | 119/159 |
| 2,910,407 | 10/1959 | Nitchner | 167/78 |
| 3,076,745 | 2/1963 | Eames | 167/53.1 |
| 3,148,649 | 9/1964 | Moore et al. | 119/1 |
| 3,502,079 | 3/1970 | Simmons et al. | 128/253 |
| 3,704,688 | 12/1972 | Wilson | 119/22 |

OTHER PUBLICATIONS

"Vaccination Against Pneumoencephalitis (Newcastle Disease) by Atomization or Nebulization in Incubators and Chick Boxes with $B_1$ Virus" by E. P. Johnson, et al., *Veterinary Medicine,* Sep. 1953, pp. 364–366, 371.

"ÜLVAFAN" (leaflet), Micron West, Inc.

ULVAFAN (8 page brochure) Salsbury Laboratories.

"Spray Vaccination: Immunizing Poultry Against Newcastle Disease", (12 page brochure) Salsbury Laboratories.

*Primary Examiner*—Henry J. Recla

*Attorney, Agent, or Firm*—Jones, Thomas & Askew

[57] ABSTRACT

Baby chicks are loaded in an open top container 32 and the container is moved into an open ended cabinet 18. In response to the movement of the container into the cabinet, a dose of vaccine is drawn from a supply 56 and delivered to a pressure chamber 41, and in response to the delivery of the dose of vaccine to the pressure chamber, air pressure is also delivered to the pressure chamber so as to eject the dose of vaccine from the pressure chamber and through at least one nozzle 42 supported in the upper portion of the cabinet. The spray ejected from the nozzle is of a droplet size large enough to fall onto the chicks in the container substantially without remaining airborne long enough to be inhaled by the chicks. The chicks are retained in the tray for a period sufficient for the normal movement of the chicks with respect to one another to cause some of the droplets of vaccine on the bodies of some of the chicks to contact and enter the eyes of some of the other chicks and for permitting some of the chicks to orally ingest some of the droplets from the bodies of other chicks.

7 Claims, 4 Drawing Figures

Fig. 2
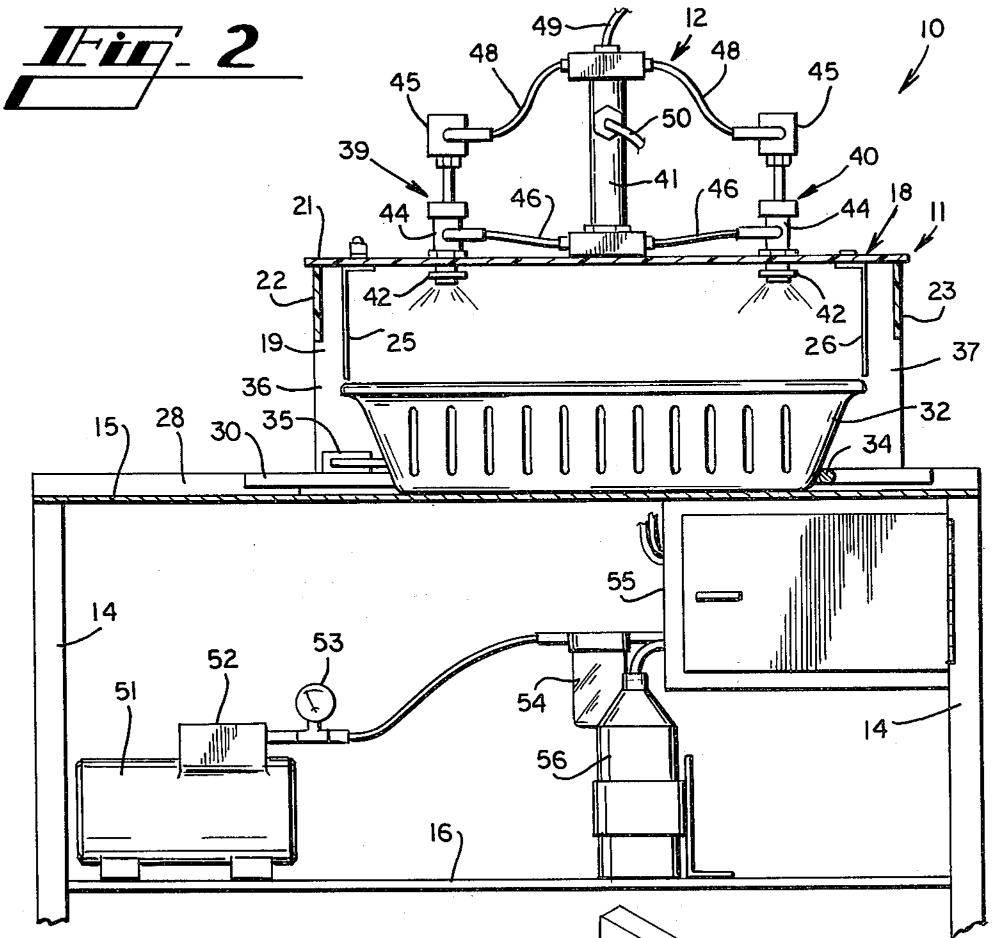
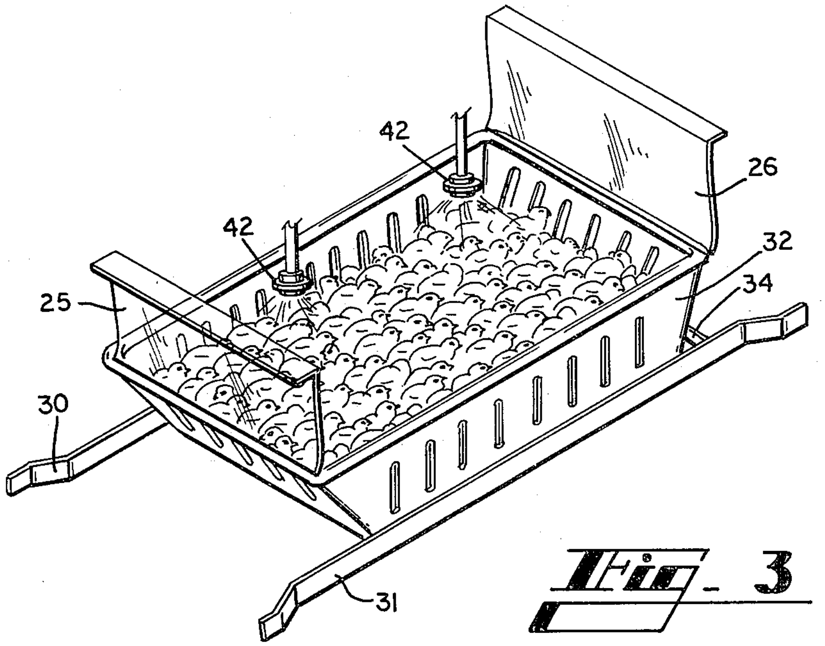
Fig. 3

POULTRY VACCINATION SYSTEM

BACKGROUND OF THE DISCLOSURE

It is customary to vaccinate poultry that is raised for commercial purposes against various respiratory diseases such as Newcastle Disease and infectious bronchitis. Usually the birds are vaccinated at the hatchery as baby chicks.

Some of the methods used to vaccinate baby chicks has been to physically inject vaccine into the body of the chick with a syringe, to spray live virus vaccine into the mouth of a chick as the upper beak is foreshortened in a "de-beaking" process, and to place a drop of vaccine with an "eye dropper" into an eye of the chick so that the vaccine enters the eye opening of the chick and passes through the nasal passage of the chick and into the respiratory system. These procedures require the chicks to be handled individually and require a long time to administer the vaccine. Also, the spraying of vaccine into the mouth of a chick sometimes results in secondary bacterial infections in the lungs of the chick and causes lung disease and death.

Another method of vaccinating chicks that was used for a short duration was to place a multiple number of the chicks in a container and form a fine mist of liquid live virus vaccine in the container about the chicks so that the chicks inhaled the the vaccine. This method of vaccinating chicks resulted in excessive vaccine reaction of the chicks and caused lung disease and death of a substantial percent of the chicks.

SUMMARY OF THE INVENTION

Briefly described, the present invention comprises a poultry vaccination system wherein baby chicks are loaded into conventional open top containers at a hatchery and the containers are moved through an open ended cabinet. A measured dose of vaccine is drawn from a supply and sprayed downwardly from within the cabinet into the open top containers and onto the chicks. Most of the spray droplets are of a size large enough to fall onto the chicks substantially without remaining airborne long enough to be inhaled by the chicks. The spray is directed in a downwardly inclined pattern so that the droplets are likely to make contact with the upper body portions of the chicks in the open top container, particularly with the eyes of the chicks. Some of the droplets come to rest on other parts of the upper body portions of the chicks, and the natural movements of the chicks in the open top container tend to spread the droplets from the upper body portions of the chicks to the eyes of the chicks, as by the head and eyes of a chick making contact with a droplet of vaccine on the upper body portion of an adjacent chick. The vaccine tends to be introduced into the sinus and respiratory system of the chick by passing from the eye of the chick into the nasal passage. Moreover, the chicks are inclined to peck at the droplets of vaccine resting on adjacent ones of the chicks, so that the vaccine is spread through the mouth to the respiratory system of some of the chicks. Furthermore, some of the chicks respond to the presence of the droplets on their upper bodies by shaking their heads and upper bodies, thereby causing the droplets to splash about adjacent ones of the other chicks, tending to help disseminate the vaccine into the eyes of adjacent ones of the other chicks.

While some of the vaccine of the spray might emerge from the spray nozzles in a fine mist, the small amount ejected from the nozzles as a mist has not been found to be sufficient to interfere with the normal respiratory function of the chicks. Moreover, the open top containers and the chicks carried thereby are removed from the spray cabinet as soon as practical after the dose of vaccine has been sprayed on the chicks so that any airborne mist is ventilated away from the chicks during the removal process.

Thus, it is an object of the present invention to provide a poultry vaccination system which rapidly and reliably administers live virus vaccine to baby chicks in measured doses, without having to individually handle each baby chick.

Another object of this invention is to provide a poultry vaccination system wherein a measured doses of vaccine is administered to a multiple number of baby chicks substantially without hazard of harming the chicks from overdosing the chicks or from manually handling the chicks.

Another object of the invention is to provide a means of spraying vaccine into the eyes of baby chicks.

Another object of the invention is to provide a system for simultaneously administering vaccine to the eyes of a multiple number of baby chicks.

Others objects, features and advantages of the present invention will become apparent upon reading the following specification, when taken in conjunction with the accompanying drawings.

BRIEF DESCRIPTION OF THE DRAWINGS

FIG. 2 is a side elevational view of the poultry vaccination cabinet, showing an open top chick container positioned in the cabinet.

FIG. 3 is a perspective illustration of an open top chick container filled with baby chicks and showing how the chick container is positioned beneath the spray nozzles and between the end curtains and side guide rails of the poultry vaccination cabinet.

DETAILED DESCRIPTION

Figure 1:
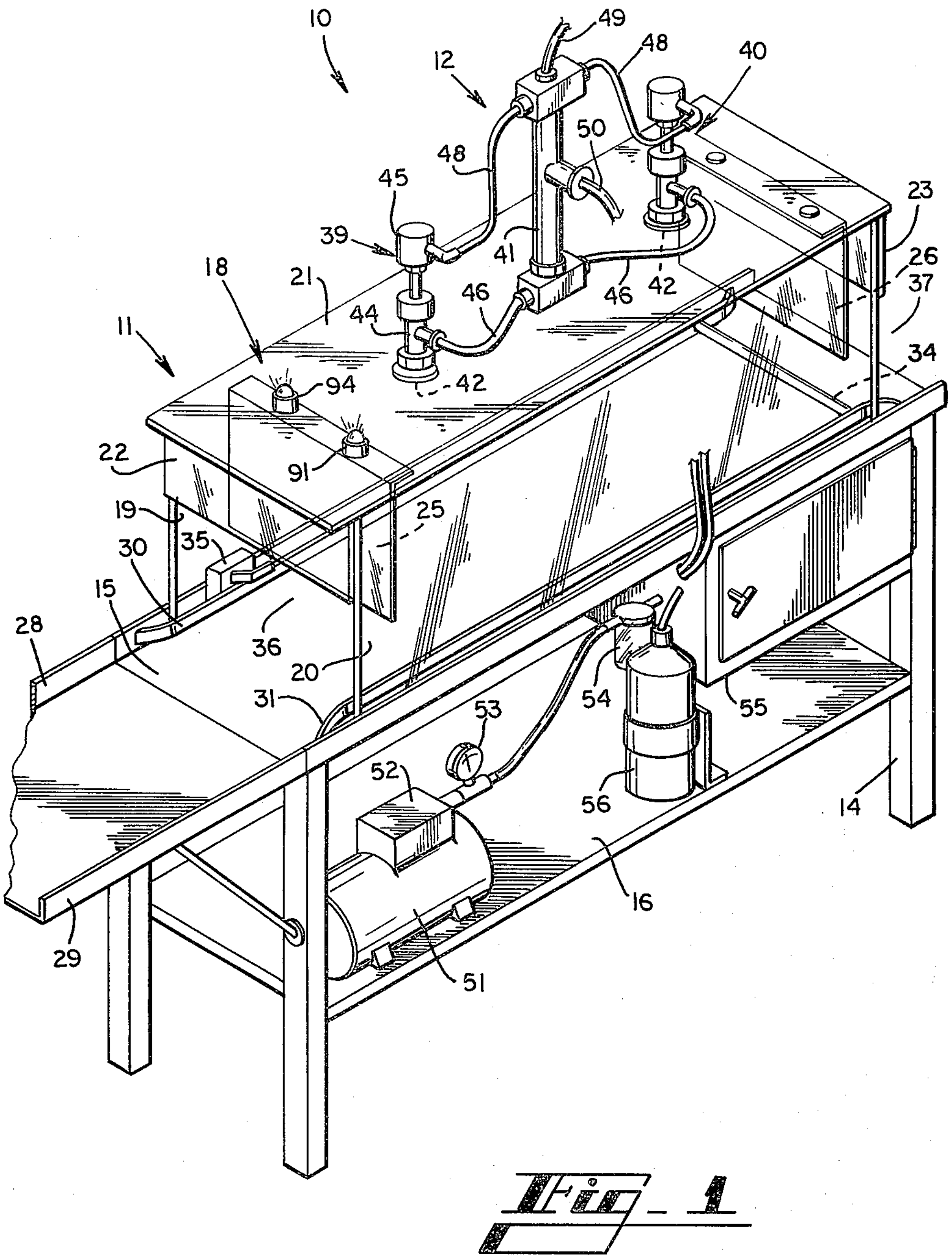
FIG. 1 is a perspective illustration of the open end poultry vaccination cabinet and related equipment of the poultry vaccination system.

Referring now in more detail to the drawings, in which like numerals indicate like parts throughout the several views, FIG. 1 illustrates the poultry vaccination system 10 which includes a cabinet assembly 11 having a vaccine control system 12 mounted thereon. The cabinet assembly 11 comprises upright support legs 14 that support at their upper ends a horizontal platform 15. A lower support platform 16 also extends between the support legs 14, and a transparent, open ended cabinet 18 is mounted on horizontal platform 15.

Cabinet 18 comprises parallel upright sidewalls 19 and 20 and a horizontal top wall 21 which merges at its side edge portions with the upper edge portions of the sidewalls. The horizontal platform 15 comprises the lower wall and conveyor platform of the cabinet 18. Upper end wall sections 22 and 23 extend a short way down from the top wall 21 at the ends of cabinet 18, so that the spaces between the lower edges of the upper end wall sections 22 and 23 and the horizontal platform 15 remain open and comprise inlet opening 36 and exit opening 37. Flexible curtains 25 and 26 are suspended from top wall 21 and are spaced inwardly of the cabinet from upper end wall sections 22 and 23. The flexible curtains 25 and 26 extend downwardly within the cabinet to a lower level than the lower edges of upper end wall sections 22 and 23. In the disclosed embodiment the cabinet 18 and flexible curtains 25, 26 are fabricated from transparent materials so that the chicks and chick containers in the cabinet can be visually observed from outside the cabinet.

Side flanges 28 and 29 extend upwardly from the edges of horizontal platform 15, and the lower edges of side walls 19 and 20 of cabinet 18 are positioned inside the side flanges 28 and 29. Guide rails 30 and 31 are attached at their ends to side flanges 28 and 29, and the end portions of the guide rails are curved so that the center portion of each guide rail extends inside the side walls 19 and 20 of the cabinet 18. Thus, the side flanges 28 and 29 and guide rails 30 and 31 define a path of movement for open top chick containers 32 (FIGS. 2 and 3). The lower portions of the chick containers 32 are of a width slightly less than the space between guide rails 30 and 31, the upper portions of the chick containers are of a length slightly less than the spaced between flexible curtains 25 and 26, and the chick containers are of a height slightly less than the distance between the surface of horizontal platform 15 and the lower edges of flexible curtains 25 and 26. A stop bar 34 is positioned at the exit opening 37 of cabinet 18, so that when a chick container 32 is moved through the inlet opening into the cabinet 18 the lower portion of the chick container will engage and its movement will be stopped by stop bar 34 and the chick container will be centrally located within the cabinet 18 (FIG. 2). Control switch 35 is positioned adjacent the entrance opening of cabinet 18 opposite from stop bar 34. Control switch 35 is positioned just inside the cabinet 18 at entrance opening 36 at the side of the path of movement of a chick container and detects the movement of a chick container 32 into the cabinet 18.

The open top chick containers 32 are of standard design and usually are to be filled with 100 baby chicks, as illustrated in FIG. 3. This contains the chicks in a crowded condition in which the chicks are in physical contact with one another.

As best illustrated in FIG. 2., the portion of the vaccine control system 12 that is mounted on cabinet 18 comprises a pair of spray nozzle assemblies 39 and 40 mounted on the top wall 21 of the cabinet, pressure chamber 41 mounted centrally between spray nozzle assemblies 39 and 40. The spray nozzle assemblies 39 and 40 each include a nozzle element 42 supported in the upper portion of cabinet 18, a valve 44 positioned above the nozzle 42, and a valve lifter 45 mounted on the valve 44. Pressure chamber 41 communicates at its lower end through branch conduits 46 with valves 44. The upper end of pressure chamber 41 communicates through branch conduits 48 with valve lifters 45. Air supply conduit 49 communicates with the upper portion of pressure chamber 41, and vaccine supply conduit 50 communicates with an upper portion of pressure chamber 41.

The nozzle elements 42 in the disclosed embodiment of the invention have a nozzle throat of approximately 0.039 inches diameter for a conical spray pattern at an angle of approximately 80°. With a back pressure of about 35 psi, the vaccine, which has a viscosity about the same as water, moves through the nozzle at a rate of about one gallon per hour.

The remaining portion of the vaccine control system is located below horizontal platform 15 and includes an oil-less compressor 51, air pressure regulator 52, air pressure gauge 53, air filter 54 and most of the elements of FIG. 4 which are located in control cabinet 55. Also, a container 56 is mounted on lower platform 16 for supplying the vaccine for the system. Air pressure regulator is to be adjusted so as to cause air at a pressure between 30 and 40 psi to be transmitted to the control system.

Figure 4:
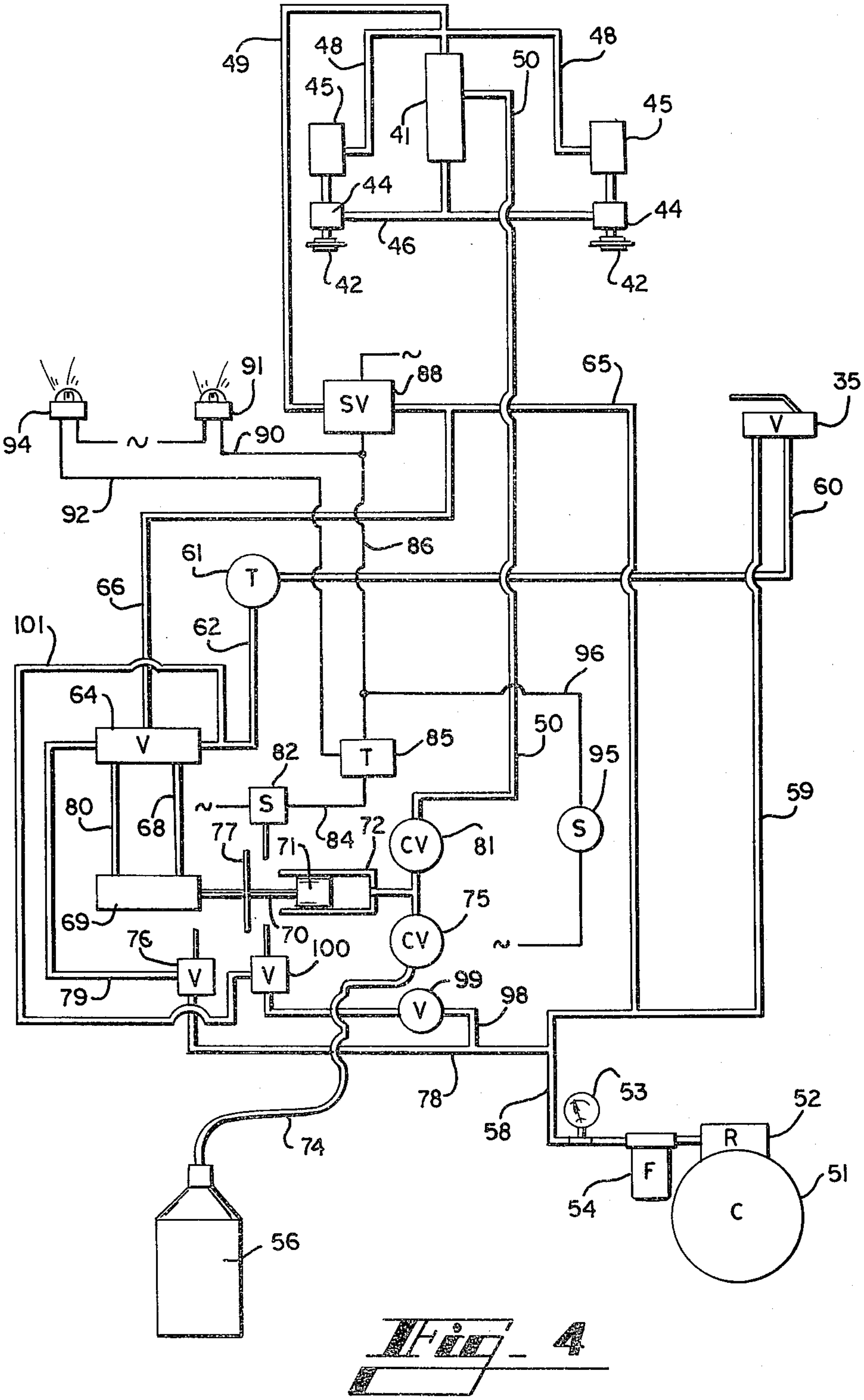
FIG. 4 is a schematic illustration of the fluid and electrical control system of the poultry vaccination system.

As illustrated in FIG. 4, control switch 35 communicates with compressor 51 through conduits 58 and 59, and when the control switch 35 is opened by the movement of a chick container 32 into the cabinet 18, air pressure communicates from valve 35 through conduit 60 to timer 61. Timer 61 sends a pulse of air through conduit 62 to one end of four-way valve 64. Four-way valve 64 communicates with air pressure line 58 through conduits 65 and 66, and when the valve 64 has been shifted by an air pulse from timer 61, air pressure communicates through conduit 68 to one end of pneumatic cylinder 69, causing cylinder rod 70 and its plunger 71 to retract. Plunger 71 comprises the piston of a piston pump, and reciprocates in cylinder 72. As plunger 71 retracts from cylinder 72, vaccine is drawn from vaccine container 56 through conduit 74 and check valve 75 into cylinder 72.

As plunger 71 reaches the end of its filling stroke, the protrusion 77 on cylinder rod 70 engages valve 76 and causes valve 76 to open. Valve 76 communicates through conduit 78 with air pressure line 58, and the other side of valve 76 communicates through conduit 79 with the other end of valve 64. Thus, when valve 76 is engaged by protrusion 77, air pressure communicates with the other end of valve 64, causing the valve to shift back to its original position. The shifting of valve 64 vents conduit 68 to the atmosphere and connects conduit 80 with air pressure in conduit 66 to change the other end of cylinder 69 with air pressure. Thus, air pressure communicates from air line 58 through conduits 65, 66 and 80 with the rear of cylinder 69, causing plunger 71 to move through its pumping stroke into cylinder 72. This causes the vaccine in cylinder 72 to move out of the cylinder and through check valve 81 and conduit 50 to the upper portion of pressure chamber 41. This one cycle of reciprocation of plunger 71, comprising a filling stroke and a pumping stroke, results in a measured dose of vaccine being drawn from vaccine container 56 and moved through conduit 50 to the upper portion of pressure chamber 41.

If the volume of the dose of vaccine is to be increased or decreased, the position of valve 76 can be moved further away from or closer to cylinder 72, so as to be engaged after a longer or shorter filling stroke of plunger 71.

As plunger 71 is finishing the delivery of its dose of vaccine, protrusion 77 of cylinder rod 70 engages electric switch 82. Conductor 84 is connected from switch 82 to timer 85. Timer 85 is connected by conductor 86 to solenoid valve 88. Solenoid valve 88 is positioned in conduit 65 and opens and closes communication between conduit 65 and conduit 49. Thus, when switch 82 is closed at the end of the vaccine pumping stroke air pressure from air line 58 communicates through conduit 65, solenoid valve 88, and conduit 49 to branch conduits 48 and to the upper portion of pressure chamber 41. Therefore, immediately after pressure chamber 41 receives a dose of vaccine, the pressure chamber 41 is charged with air under pressure. Additionally, branch conduits 48 charge the valve lifters 45 with air pressure, causing the valve lifters to open valves 44. This results in vaccine being urged through branch conduits 46 and through nozzles 42 into cabinet 18. The timer 85 holds solenoid valve 88 open for a period sufficient to discharge the dose of vaccine from pressure chamber 41. When timer 85 times out, solenoid valve 88 closes and the pressure in pressure chamber 41 dissipates for the most part through valves 44. Some of the pressure of the system is vented back through solenoid valve 88.

Conductor 90 is connected to conductor 86 and to indicator light 91. Thus, when solenoid valve 88 is open in response to timer 85, indicator light 91 is illuminated, indicating to the operator that vaccine is being sprayed from nozzles 42 into the open top chick container 32 and onto the upper body portions of the chicks in the container. Timer 85 is also connected to conductor 92, and conductor 92 is connected to another indicator light 94. When timer 85 times out, indicator light 94 is illuminated. This indicates to the operator that the spray cycle has been completed and the system is ready for another load of chicks.

It is desirable to flush and clean the vaccine from the system at the end of a work period. During the cleaning cycle the vaccine container 56 is replaced with a container of cleaning liquid. Electric switch 95 is connected by its conductor 96 to conductor 86 so that the timer 85 can be by-passed in the electrical circuitry. When switch 95 is closed, a continuous signal is provided to solenoid valve 88, thus supplying a continuous charge of air pressure to pressure chamber 41. In the meantime, the conduit 98 communicates with conduit 78, and manual valve 99 in conduit 98 is opened so that a continuous charge of air is supplied to air valve 100. Air valve 100 is located in the path of travel or protrusion 77, so that it is actuated as plunger 71 delivers a dose of liquid through the system. When valve 100 is opened by protrusion 77, air pressure communicates from air line 58 through conduit 78, conduit 98, manual valve 99, valve 100 and conduit 101 to the end of valve 64. Thus, valve 64 shifts so as to supply a charge of air pressure from air line 58 and conduits 65 and 66 through valve 64 through conduit 68 and into air cylinder 69, whereupon plunger 71 is retracted for a filling stroke. When protrusion 77 engages valve 76, the valve 76 opens and shifts valve 64 so as to move plunger 77 in the opposite direction as previously described. With this arrangement, plunger 71 will continue to reciprocate until valve 99 is closed. Thus, air will be continuously supplied to pressure chamber 41 and continual doses of cleaning liquid will be supplied to pressure chamber 41, causing the system to be continuously cleaned.

While horizontal platform 15 has been indicated as being a flat work surface, it will be understood by those skilled in the art that platform 15 can comprise a conveyor belt, a roller conveyor or other means for guiding and/or moving chick containers in a horizontal direction through transparent open ended cabinet 18. Additionally, stop bar 34 is illustrated as being a rigid member extending between guide rails 30 and 31; however, it should be understood that the stop bar can comprise a movable member that enters the path of the chick containers so as to stop the movement of the chick containers through the cabinet, and then retracts from the path of the chick containers so as to permit the chick containers to move out the exit opening of the cabinet.

When the spray cycle has been completed, it is desirable to remove the chick containers from the cabinet so that the next chick container can be inserted into the cabinet. The sprayed chick containers usually are stacked one atop the other and the side vent openings in the chick containers permit proper ventilation for the chicks.

After the spray cycle has been completed, the droplets of vaccine will have been sprayed to the upper body portions of the chicks in each chick container. Some of the droplets will make direct contact with the eyes of the chicks, thus causing some of the chicks to be directly vaccinated. Other droplets will come to rest on the upper body portions of the chicks. The natural movements of the chicks in the chick container and the crowded conditions of the chicks in the container result in some of the droplets being rubbed from the upper body portions of the chicks into the eyes of adjacent chicks. Additionally, some of the chicks respond to the spray by shaking their heads and upper body portions. This causes some of the droplets to be splashed into the eye openings of adjacent chicks. When the vaccine enters the eye opening of a chick, it tends to migrate through the nasal passages of the chick to be ingested by the chick. Also, some of the chicks tend to peck at droplets of vaccine that are supported on the upper body portions of adjacent chicks. This results in some of the vaccine being ingested orally by the chicks. It is desirable to retain the chicks in the chick containers for a period sufficient for the natural body motions and instincts of the chicks to disseminate the vaccine among the chicks in this manner.

While this invention has been described in detail with particular reference to a preferred embodiment thereof, it will be understood that variations and modifications can be effected within the scope and spirit of the invention as described hereinbefore and as defined in the appended claims.

I claim:

1. A method of vaccinating poultry comprising placing a multiple number of chicks in an open top container in a crowded condition in which the chicks are in physical contact with one another, moving the container along a horizontal path until the container is located beneath at least one spray nozzle, and in response to the container moving toward its position beneath the spray nozzle ejecting a vaccine spray from the nozzle downwardly onto the upper portions of and into the eyes of the chicks in a droplet size large enough to fall onto the chicks substantially without remaining airborne long enough to be inhaled by the chicks, removing the container from beneath the spray nozzle, and retaining the chicks in the container for a period sufficient for the normal movement of the chicks with respect to one another to cause some of the droplets of vaccine on the bodies of some of the chicks to make contact with the bodies of adjacent chicks.

2. The method of claim 1 and wherein the step of moving the container along a horizontal path until the tray is located beneath at least one spray nozzle comprises moving the tray through one open end of and into an open ended cabinet to a position between movable curtains at the open ends of the cabinet and against an abutment.

3. The method of claim 1 and wherein the step of moving the container along a horizontal path until the container is located beneath at least one spray nozzle comprises moving the container through one open end of and into an open ended transparent cabinet against an abutment, and wherein the step of removing the container from beneath the spray nozzle comprises moving the container through the other open end of and out of the open ended transparent cabinet.

4. The method of claim 1 and wherein the step of ejecting a vaccine spray from the nozzle downwardly onto the chicks comprises filling a chamber which communicates with the spray nozzle with a measured dose of vaccine while communication between the chamber and the nozzle is closed, charging the chamber with air pressure and opening communication between the chamber and the nozzle so that the dose of vaccine moves through the nozzle.

5. The method of claim 1 and wherein the step of ejecting a vaccine spray onto the chicks in response to the container moving toward its position beneath the spray nozzle comprises drawing a measured dose of vaccine from a supply, and in response to having drawn the measured dose of vaccine moving the measured dose of vaccine to a chamber which communicates at its lower end with the spray nozzle, and in response to having moved the measured dose to the chamber charging the chamber with air pressure and opening between the chamber and the nozzle so that the dose of vaccine moves through the nozzle.

6. Apparatus for vaccinating poultry comprising an open ended cabinet including a top and opposed sides and defining a horizontal path extending therethrough from one open end to the other open end, flexible curtains partially closing the open ends of said cabinet, a stop member positioned at one open end of said cabinet for stopping the movement of open top chick containers moved into the cabinet through the other open end, at least one spray nozzle supported in the upper portion of said cabinet for spraying vaccine downwardly into the chick containers in a droplet size large enough to fall on chicks in the chick containers substantially without remaining airborne long enough to be inhaled by the chicks, spray control means for moving vaccine through said spray nozzle, said spray control means comprising pump means having an inlet for communicating with a supply of liquid vaccine and an outlet, a pressure chamber having an inlet in communication with the outlet of said pump means and an outlet in communication with said spray nozzle, air pressure supply means, said pressure chamber including an inlet in communication with said air pressure supply means, switch means for detecting the movement of an open top chick container into said cabinet, air control means responsive to said switch means for actuating said pump means to move a dose of vaccine from the supply to said pressure chamber, and means responsive to said pump means moving a dose of vaccine to said pressure chamber for charging said pressure chamber with air from said air pressure supply means, whereby the dose of vaccine in said pressure chamber is urged by the air pressure in said pressure chamber to move through said nozzle and downwardly in said cabinet onto the chicks in an open top chick container in said cabinet.

7. Apparatus for vaccinating poultry by contacting the eyes of chicks with a vaccine comprising means for supporting an open top chick container beneath at least one spray nozzle, control means responsive to the movement of the chick container to a position beneath the spray nozzle for drawing a measured dose of vaccine from a supply, and moving the dose of vaccine through said spray nozzle to form the vaccine in a droplet size large enough to fall onto the chicks substantially without remaining airborne long enough to be inhaled by the chicks.

* * * * *